(12) United States Patent
Rosenberg et al.

(10) Patent No.: US 7,393,840 B2
(45) Date of Patent: Jul. 1, 2008

(54) FORMULATION BASED ON HEPARIN, GLYCOSAMINOGLYCAN OR HEPARINOID, USE OF THE FORMULATION AND THE FORMULATION BASE

(75) Inventors: Jörg Rosenberg, Ellerstadt (DE); Jörg Breitenbach, Mannheim (DE); Dieter Herr, Altrip (DE); Volker Laux, Mainz (DE); Robert Heger, Heidelberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 440 days.

(21) Appl. No.: 10/296,441

(22) PCT Filed: May 29, 2001

(86) PCT No.: PCT/EP01/06115

§ 371 (c)(1),
(2), (4) Date: Nov. 25, 2002

(87) PCT Pub. No.: WO01/91729

PCT Pub. Date: Dec. 6, 2001

(65) Prior Publication Data

US 2003/0161884 A1  Aug. 28, 2003

(30) Foreign Application Priority Data

May 30, 2000 (DE) .............................. 100 26 699

(51) Int. Cl.
*A61N 31/747* (2006.01)
(52) U.S. Cl. ..................................... 514/56; 514/772.3
(58) Field of Classification Search ........................ None
See application file for complete search history.

(56) References Cited

U.S. PATENT DOCUMENTS

| 4,656,161 A | * | 4/1987 | Herr ............................ 514/56 |
| 4,925,673 A | | 5/1990 | Steiner et al. |
| 5,346,701 A | | 9/1994 | Heiber et al. |

(Continued)

FOREIGN PATENT DOCUMENTS

WO          99/42086          8/1999

(Continued)

OTHER PUBLICATIONS

XP-000886866, Yeh et al., Phar. Res.,vol. 11, No. 8, 1994.

(Continued)

*Primary Examiner*—Michael G. Hartley
*Assistant Examiner*—Eric E. Silverman
(74) *Attorney, Agent, or Firm*—Novak Druce + Quigg LLP

(57) ABSTRACT

The present invention relates to formulations based on at least one heparin, glycosaminoglycan or heparinoid and on a formulation base with a lipid component and a polymer component. The use of this formulation as drug form for oral administration of at least one heparin, glycosaminoglycan or heparinoid, and also a process for producing the formulations by mixing the formulation components to form a plastic mixture and, where appropriate, to manufacture the formulations as drug form, advantageously using melt extrusion, are described. The lipid component advantageously has active ingredient-promoting properties, while the polymer component is soluble or swellable. At least parts of the lipid component are embedded in a polymer matrix, preferably in the form of a molecular dispersion. The formulations can form emulsions in water or aqueous liquids.

21 Claims, 1 Drawing Sheet

U.S. PATENT DOCUMENTS 5,626,869 A    5/1997   Nyqvist et al.
5,707,648 A *  1/1998   Yiv .............................. 424/450
6,309,663 B1 * 10/2001  Patel et al. .................. 424/450
6,387,401 B2   5/2002   Rosenberg et al.

FOREIGN PATENT DOCUMENTS

WO    99/44642     10/1999
WO    01/01960     1/2001

OTHER PUBLICATIONS

Serajuddin et al., Bioavailability Enhancement of Poorly Water-Soluble Drugs by Solid Dispersion in Surface Active and . . . , Journees Galeniques, 1997, pp. 43-50.

Leone-Bay et al., Synthesis and Evaluation of Compounds that Facilitate the Gastrointestinal Absorption of Heparin, J Med Chem, 1998, vol. 41(7), pp. 1163-1171.

Bachynsky et al., Factors Affecting the Efficiency of a Self-Emulsifying Oral Delivery System, Drug Development and Industrial Pharmacy, 1997, vol. 23(8), pp. 809-816.

* cited by examiner

FORMULATION BASED ON HEPARIN, GLYCOSAMINOGLYCAN OR HEPARINOID, USE OF THE FORMULATION AND THE FORMULATION BASE

The present invention relates to formulations based on at least one heparin, glycosaminoglycan or heparinoid and on a formulation base with a lipid component and a polymer component; to the use of this formulation as drug form for the oral administration of at least one heparin, glycosaminoglycan or heparinoid; the invention also describes a process for producing the formulations by mixing the formulation components to form a plastic mixture and, where appropriate, to manufacture the formulations as drug form; and to the use of a formulation base in the oral administration of heparins, glycosaminoglycans or heparinoids.

The advantages of the oral administration, which is pleasant per se for the patient, of active ingredients are often reduced by measures which must be taken with a view to adequate adsorption of an active ingredient in the gastrointestinal tract. Thus, relatively high daily doses which are divided into several administrations may be necessary to obtain therapeutically effective blood levels. Proposed solutions disclosed in the pharmaceutical technology sector involve the active ingredients being formulated together with selected excipients. These are normally nonionic surfactants with quite high HLB values, e.g. Cremophor®, Tween®, etc.

Although these excipients are commonly designated chemically inert, they are known to have disadvantages which may become evident in particular at higher dosages through local and/or systemic toxicity.

Besides local irritation, e.g. of the bowel wall, it is not possible to preclude unwanted side effects of these stabilizers outside the gastrointestinal tract, owing to the absorption of these substances.

It is known that emulsions are capable of colloidal solubilization of active ingredients of low solubility, by which means it is possible to improve the bioavailability of such active ingredients. Emulsions which can be administered parentally normally use emulsifying phospholipids, in particular lecithins. However, because of the inadequate chemical stability of the phospholipids, these emulsions may be associated with considerable storage stability problems. In addition, the preparation of such emulsions is complicated. Thus, it may be necessary to homogenize the phospholipids in water together with other emulsion constituents, for example lipids or lipid derivatives, under high pressure, e.g. under several 100 bar.

Besides the liquid emulsions described above, "solid" emulsions are also known. These formulations are generally referred to as self-emulsifying systems because they dissolve in aqueous systems to form an emulsion (cf. M. O. Bachynsky et al., "Factors Affecting the Efficiency of a Self-Emulsifying Oral Delivery System", Drug Development and Industrial Pharmacy, 23 (8), (1997) 809-816). The solubilization-promoting excipients discussed at the outset are also mainly used in these cases, which entails the known disadvantages. Besides the low molecular weight surfactants, e.g. Tween®, which are particularly used, self-emulsifying systems based on polymeric glyceride surfactants are also described (A.T.M. Serajuddin, "Bioavailability Enhancement of poorly Water-Soluble Drugs by Solid Dispersion in Surface Active and Self-Emulsifying Vehicles", Bulletin Technique Gattefossé, No. 90, (1997), pp. 43-50). These polymeric glycerides may act as surfactant because of their high HLB values (e.g. Gelucire® 44/14 with an HLB of 14). Because of their semisolid consistency, many of these formulations must be packed into gelatin capsules. This applies in particular to the use of the usually low-melting glyceride surfactants.

However, even freely soluble active ingredients may be difficult to absorb in some circumstances. In such cases, WO 99/42086 proposes employing absorption promoters with HLB values of more than 8, especially polyglycosylated glycerides, e.g. the Gelucire® which has already been mentioned. Freely soluble active ingredients of this kind include, with the heparins, active ingredients which have for many years represented a standard therapy especially in the area of thrombotic indications. Despite very intense efforts to overcome the well-known extremely low bioavailability of heparins after oral administration, it has not to date been possible to develop a marketable product. It is true that after oral administration of heparin the coagulation times found in the APTT test are comparable to those after intravenous administration, when heparins are encapsulated in certain protinoid [sic] microspheres composed of linear thermal condensation polymers of mixed amino acids (cf. U.S. Pat. No. 4,925,673) or are given at the same time as certain synthetic lipid derivatives (e.g. β-(hydroxybenzoyl)amino-octanoic acid; J. Med. Chem. 41, (1998), 1163). The disadvantage of these formulations is that extremely large amounts of excipients and active ingredients must be administered, so that the formulations can usually be taken only in liquid form.

The object on which the present invention is based, of providing drug forms for oral administration of heparins, glycosaminoglycans or heparinoids, is surprisingly achieved by formulations whose formulation base has a lipid component and a polymer component.

The present invention therefore relates to formulations based on i) at least one heparin, glycosaminoglycan or heparinoid and, where appropriate, other active ingredients and a formulation base with
ii) a lipid component;
iii) a polymer component; and
iv) where appropriate other pharmaceutically acceptable excipients.

The term "formulation" means in the framework of the present invention a mixture composed of components i), ii), iii) and, where appropriate, iv).

The term heparin describes a group of sulfated (sulfonated) mucopolysaccharides which are also referred to as glycosaminoglycans. The structural characteristics of heparins are disaccharide units composed of α-1,4-glycosidically linked D-glucosamine and L-iduronic acid units, and disaccharide units composed of α-1,4-glycosidically linked D-glucosamine and D-glucuronic acid units. Both the position and the number of the sulfate groups (sulfo groups) is variable. They may be bonded via oxygen (O-sulfated) and via nitrogen (N-sulfated). Iduronic acid residues are frequently 2-O-sulfated, and glucosamine residues are frequently N-sulfated and, where appropriate, also 6-O-sulfated. Glucuronic acid residues by contrast are frequently unsulfated. The disaccharide units are in turn connected together α-1,4-glycosidically to form heparin molecules. The number and arrangement of these disaccharide units may likewise vary, so that the term heparin describes a large number of structurally different molecules which can be distinguished, for example, by elemental analysis or on the basis of their chain length, their molecular weight or their charge. The term heparin designates in particular mixtures of structurally different heparin molecules of the type described above (α-heparins), which may also, where appropriate, comprise other constituents such as the so-called β-heparin, also called chondroitin sulfate B or dermatan sulfate, and/or other cell constituents, especially proteins. Mixtures of this type may likewise be characterized by the aforementioned parameters, it being customary to state averages and/or distributions, for example lower and/or upper limits.

Heparins may exist as free acid or in the form of physiologically tolerated salts. The sodium, calcium and magnesium salts are preferred.

Heparins of natural origin, modified where appropriate, are generally administered. Heparins from the lung, liver or intestinal mucosa of cattle or pigs can be used, with heparins from pig intestinal mucosa, and from bovine lung frequently being used.

The molecular weights of heparin molecules are usually in the range from 200 to 30 000 Da. Heparins which can be used as active ingredient according to the invention may cover this entire molecular weight range or only parts thereof, in particular the low molecular weight range. Preference is given to so-called LMW heparins, i.e. mixtures of heparin molecules with weight average molecular weights of about 500 to about 10 000 Da. Whereas unfractionated heparins with a broad molecular weight distribution usually have weight average molecular weights of about 10 000 to 17 000 Da, the weight average molecular weights of the LMW heparins are distinctly lower, usually about 2 000 to 8 000, and in particular, about 3 000 to about 8 000, about 4 000 to about 6 000 or about 4 000 to about 5 000 Da.

Low molecular weight heparins which can be used according to the invention are obtained by fractionation or, preferably, fragmentation, e.g. depolymerization, of heparins with a broad molecular weight distribution or higher weight average molecular weight. The heparins used as starting materials are, in particular, those obtained from natural sources and, especially, their calcium or sodium salts. Fractionation is possible by ethanol extraction, and fragmentation preferably by controlled, partial chemical or enzymatic (e.g. heparinase) or physical (e.g. ultrasound) cleavage of heparins. The chemical cleavage is possible, for example, with sodium nitrite, and specific enzymes, usually bacterial heparinases, for example from flavobacterium, are available for the enzymatic cleavage.

Glycosaminoglycans are negatively charged polysaccharides (glycans) which consist of 1,4-linked units of disaccharides in which uronic acid, for example D-glucuronic acid and L-iduronic acid, is glycosidically connected to the 3 or 4 position of an N-acetylated aminosaccharide (glycosamine).

The term heparinoids describes a group of substances with a heparin-like effect, i.e. heparinoids inhibit the coagulation of blood and the development of thromboses. These include, for example, sulfated vegetable oligo- and polysaccharides, e.g. polysulfates prepared from alginic acid, pectins, xylans, starches and dextrans, or sulfated animal glycosaminoglycans. Particular mention should be made of pentosan polysulfates, e.g. sodium pentosansulfonate, xylan sulfate, e.g. β-1,4-D-xylan 2,3-bis(hydrogen sulfate), xylan poly(hydrogen sulfate) and sodium salts thereof, dextran sulfates, chitin sulfates, chondroitin polysulfates, also called mucopolysaccharide polysulfates, polyvinylsulfonic acids, also called polyethylenesulfonic acids, e.g. sodium apolate, polygalacturonic acid sulfate (methyl ester methyl glucoside), alginate sulfates, e.g. sodium alginate sulfate and polymannuronic acid sulfate.

Heparinoids either may be obtained from natural sources or they are prepared semisynthetically or completely synthetically, normally by sulfating the aforementioned vegetable or animal polysaccharides, for example reacting with chlorosulfonic acid, and neutralizing liberated hydrochloric acid with bases.

It is common to heparins and heparinoids that although their solubility in water is good, they are only slightly absorbed from the gastrointestinal tract. The inadequate absorbability is attributable in particular to the fact that heparins and heparinoids are negatively charged. The formulation of the invention is suitable in a particularly advantageous manner for precisely this type of active ingredient, i.e. substances which are soluble in water and, in particular, negatively charged, especially corresponding sulfated polysaccharides. Active ingredients are soluble in water in the sense of the invention especially when one part of the active ingredient can be dissolved in not more than 10 to 30 parts, preferably in not more than 1 to 10 parts and, in particular, in less than 1 part of water.

The active ingredient component i) of the, preferably solid, formulations of the invention comprises at least one anticoagulant of the heparin, glycosaminoglycan or heparinoid type and may comprise other anticoagulants of the heparin, glycosaminoglycan or heparinoid type as well as anticoagulants of other types, such as coumarin derivatives, e.g. warfarin, phenprocoumon and acenocoumarol, and other active ingredients of differing effect, such as ergotamines and dihydroergotamines, e.g. dihydroergotamine mesilate, thrombin inhibitors, e.g. argatroban and melagatren [sic]. One embodiment of the present invention comprises monopreparations which comprise a heparin, glycosaminoglycan or heparinoid as active ingredient component.

The active ingredient component usually constitutes 1 to 60% by weight, preferably 5 to 40% by weight, and in particular 10 to 30% by weight of the formulation. Unless otherwise indicated, data in % by weight relate to the total weight of the formulation.

The formulation base of formulations of the invention comprises pharmaceutically acceptable excipients, namely at least one lipid, at least one polymer and, where appropriate, other pharmaceutically acceptable excipients. Pharmaceutically acceptable excipients are those which are known to be usable in the pharmaceutical sector, especially those listed in the relevant pharmacopeias (e.g. DAB, Ph. Eur., BP, NF) and also other excipients whose properties do not stand in the way of pharmaceutical use.

The lipid component of formulations of the invention comprises at least one lipid, which is intended to refer also to lipid derivatives and lipid-containing mixtures.

The term lipid is a collective designation for fats and fat-like substances. The similarity to fats is defined in particular by the solubility characteristics. Accordingly, fat-like substances such as fats themselves are, for example, practically insoluble in water. Substances are insoluble in water in the sense of the invention especially when at least 1 000 to 10 000 parts, and preferably at least 10 000 parts of water are necessary to dissolve one part of substance. They are also referred to as lipophilic or hydrophobic.

Preferred lipids are those which the organism to be treated can assimilate, that is to say, for example, can take up and, where appropriate, metabolize. In this sense, those lipids and lipid derivatives which can be taken up via the gastrointestinal tract implement a particular embodiment of the present invention. Natural lipids and derivatives of natural lipids, which may be of vegetable or animal origin, are preferred.

It is particularly preferred for at least one lipid of the lipid component to be selected from endogenous lipids, in particular glycerides and fatty acids or derivatives thereof. The endogenous lipids include in particular lipids based on fatty acids with an even number of carbon atoms.

The term fatty acid refers to a group of aliphatic saturated or unsaturated carboxylic acids. The chains are usually unbranched and have 6 to 30, preferably 8 to 22, and in particular 8 to 18, carbon atoms. The saturated fatty acids include, for example, caproic acid, enanthic acid, caprylic acid, pelargonic acid, capric acid, undecanoic acid, lauric acid, tridecanoic acid, myristic acid, pentadecanoic acid, palmitic acid, margaric acid, stearic acid, nonadecanoic acid, arachidic acid, behenic acid, lignoceric acid, cerotic acid and melissic acid. The unsaturated fatty acids may be unsaturated one or more times, in particular unsaturated once, twice, three times, four times, five times or six times. Examples of singly unsaturated fatty acids include palmitoleic acid, oleic acid and erucic acid, of doubly unsaturated fatty acids include sorbic acid and linoleic acid, of triply unsaturated fatty acids include linolenic acid and eleostearic acid, of quadruply unsaturated fatty acids include arachidonic acid, of quintuply unsaturated fatty acids include clupanodonic acid, and of sextuply unsaturated fatty acids include docosahexaenoic acid.

Singly or multiply unsaturated fatty acids are preferred, especially oleic acid, palmitoleic acid, erucic acid, linoleic acid, linolenic acid.

The term glycerides refers to esters of glycerol. Depending on the number of ester groups, reference is made to mono-, di- and triglycerides. The acid residue in a monoglyceride may be at position 1 or 2 and the acid residues of di- and triglycerides may be identical or different and be distributed in every conceivable way over the three possible positions of glycerol. The acid residues are preferably the fatty acids described above. Examples of monoglycerides include glycerol monobehenate, glycerol monocaprate, glycerol monococoate, glycerol monoerucate, glycerol monoisostearate, glycerol monolanolate, glycerol monolaurate, glycerol monolinoleate, glycerol monomyristate, glycerol monooleate, glycerol monopalmitate, glycerol monoricinoleate, glycerol monostearate, of the diglycerides include glycerol dicaprylate, glycerol dilaurate, glycerol dimyristate, glycerol dioleate, glycerol dipalmitate and glycerol distearate, of the triglycerides include glycerol tricaprylate, glycerol trilaurate, glycerol trimyristate, glycerol trioctanoate, glycerol trioleate, glycerol triricinoleate and glycerol tristearate.

Preference is given to mono-, di- and triglycerides with unsaturated fatty acid residues, in particular the fatty acid residues which can preferably be used according to the invention, especially glycerol monooleate, glycerol dioleate, glycerol trioleate.

The lipid component of formulations of the invention preferably comprises at least one of the lipids described above or a mixture of at least two of the lipids described above, and it may contain other lipids of this type and also of other types.

In one embodiment of the present invention, the lipid component consists of one of the lipids described above.

In another embodiment of the present invention, the lipid component consists of a lipid mixture of at least two of the lipids described above, in particular of a fatty acid mixture, a glyceride mixture or a fatty acid/glyceride mixture.

The derivatives of natural lipids, which may be of vegetable or animal origin, include in particular those natural lipids which have been chemically and/or physically treated. A suitable chemical treatment is, for example, hydrogenation of unsaturated fatty acids or fatty acid residues in glycerides. A suitable physical treatment is, for example, fractionation of natural lipid mixtures.

The lipids which can be used according to the invention also include lipid-containing natural substance extracts which, besides lipid, may also contain other constituents. Mention should be made here in particular of the lipids and lipid mixtures listed in relevant pharmacopoeias, and derivatives thereof, such as vegetable oils or animal fats, e.g. olive oil, castor oil, sesame oil, peanut oil, almond oil, linseed oil, cocoa butter, sunflower oil, medium chain-length triglycerides (triglycerida mediocatenalia), calcium behenate, glycerol monostearate, medium chain-length partial glycerides (partialglycerida mediocatenalia), longer-chain partial glycerides (partialglycerida longicatenalia), which may also, where appropriate, be hydrogenated or refined, such as hydrogenated castor oil or refined castor oil. Once again, lipids with a content of unsaturated fatty acids or fatty acid residues are preferred.

In a particular embodiment, the lipid component has an HLB not exceeding 12, preferably not exceeding 8, and in particular not exceeding 5. The HLB system (hydrophilic lipophilic balance system) assigns numerical values to surface-active substances; the HLB values of lipophilic substances are low, and those of hydrophilic ones are higher (Fiedler, H. B., Lexikon der Hilfsstoffe für Pharmazie, Kosmetik, und angrenzende Gebiete, 4th edition, Aulendorf: ECV-Editio-Cantor-Verlag (1996)). In particular, the lipid component is insoluble or of only low solubility in water. Accordingly, this embodiment can be implemented in particular with the aforementioned fatty acids and glycerides.

In another preferred embodiment, the lipid component has a melting point not exceeding 50° C., preferably not exceeding 40° C., and in particular of less than 30° C. Accordingly, this embodiment can be implemented in particular with fatty acids such as tridecanoic acid, lauric acid, elaeostearic acid, preferably undecanoic acid, capric acid, erucic acid, in particular pelargonic acid, caprylic acid, enanthic acid, caproic acid, isostearic acid, oleic acid, palmitoleic acid, linoleic acid, linolenic acid, arachidonic acid, clupanodonic acid and docosahexaenoic acid, and glycerides such as glycerol monolaurate, glycerol monolinoeate, glycerol monooleate, glycerol monopalmitate, glycerol monoricinoleate, glycerol dioleate, glycerol trioleate and glycerol triricinoleate.

It is particularly preferred for at least part of the lipid component and at least part of the polymer component to form a molecular dispersion in the formulations of the invention. If the lipid content is greater than the polymer content, there is said to be a molecular dispersion of the polymer in the lipid. The lipid content is preferably less than the polymer content, in which case there is said to be a molecular dispersion of the lipid in the polymer.

The term "molecular dispersion" is known to the skilled worker and essentially describes systems in which a substance, in the present case at least part and preferably the predominant part of the lipid or polymer component, is homogeneously dispersed in a solvent. In such cases, the solvent usually forms a matrix which, according to the invention, is formed by the polymer or lipid component or at least by a predominant part of the polymer or lipid component. The content of lipid crystals in a formulation of the invention is usually below 12% and, in particular, below 5%. Statements concerning contents of crystals are based on the total amount of the respective component.

In a particular embodiment, molecular dispersion systems are solid, in which case they are referred to as solid solutions.

A formulation of the invention which is essentially free of lipid crystals represents a particular embodiment of the present invention. This state corresponds to the maximum possible homogenization of the lipid or polymer in the matrix. There are no interfaces in the molecular dispersion system.

In another particular embodiment, at least part of the active ingredient component is in the form of a molecular dispersion. The content of active ingredient crystals in a formulation of the invention is usually less than 12% and, in particular, less than 5%. These formulations include, in particular, those which are essentially free of active ingredient crystals. This state corresponds to the maximum possible homogenization of the active ingredient in the formulation base.

Formulations of the invention which are essentially free of lipid and active ingredient crystals and, in particular, those in which there are essentially no crystalline contents of any constituent (essentially amorphous or crystal-free formulations) represent another particular embodiment of the present invention. This state corresponds to the maximum possible homogenization of the formulation components. There are no interfaces in the formulation which is a molecular dispersion.

Known analytical methods can be used to investigate the state of such molecular dispersions, in particular solid solutions, for example differential scanning calorimetry (DSC) or wide angle X-ray scattering measurements (WAXS measurements). The DSC analytical measurement of a molecular dispersion lacks the melting peak which occurs with the crystalline pure substance and is usually endothermic. Another possibility for identifying a molecular dispersion is the reduction in intensity and/or absence of typical X-ray diffraction signals in the WAXS analysis.

The content of the lipid component in the formulation is usually from 3 to 50% by weight, preferably 6 to 35% by weight, and in particular 11 to 30% by weight.

One criterion for establishing the optimal amount of lipid is the homogeneity of the formulation of the invention in the melt. Especially in relation to the upper limit, a homogeneous incorporation of the lipid into the melt without phase separation ought to be ensured.

In a particular embodiment of the present invention, the content of the lipid component based on the polymer component, does not exceed 40% by weight, preferably does not exceed 30% by weight, and in particular does not exceed 25% by weight.

The polymer component of the formulations of the invention can also be understood as polymeric binder which at least partly forms a polymer matrix. Binders for the purpose of the invention are solid, meltable solvents. The polymer matrix serves especially to take up, and in particular dissolve, at least part of the lipid component. This preferably leads to the formation of molecular dispersions. In this regard, reference is made to the above statements in connection with the lipid component.

The polymer component is preferably at least partly soluble or swellable in a physiological environment, i.e. in particular in the gastrointestinal tract, especially in the upper region of the small intestine and preferably in the duodenum. Swelling means essentially a process in which the volume and/or shape of a solid body, for example a solid formulation of the invention, change on exposure to liquids, vapors and gases, that is to say, in accordance with the invention, usually on exposure to body fluids and in particular those of the gastrointestinal tract. Swellable or soluble applies in particular to hydrophilic polymers able to accumulate water at least on the surface and/or take up water between the polymer chains, mainly by absorption. Limited swelling usually results in gel formation, which is why polymers capable of limited swelling and usable according to the invention can be selected from the polymers commonly known as gel formers. Unlimited swelling usually leads to the formation of solutions or colloidal solutions, which is why polymers capable of unlimited swelling and usable according to the invention can be selected from the polymers in the physiological environment, in particular in the body fluids of the gastrointestinal tract which form at least colloidal solutions. It must be taken into account, in particular, in relation to the gastrointestinal tract, that there may be local differences in the physiological conditions, especially the pH. If it is preferred, for example, for the active ingredient to be absorbed mainly in the duodenum, it may be advantageous for the polymer component to be swellable under the conditions prevailing in the duodenum. In particular, it may be advantageous for only slight or preferably essentially no swelling to take place in the preceding sections of the gastrointestinal tract, especially in the stomach. However, it may be remarked at this point that such behavior of formulations of the invention after administration can also be ensured with other means, in the case described above for example with coatings resistant to gastric juice or multilayer formulations in which the innermost layers containing active ingredient are exposed to swelling or dissolving only at the required site.

In a particular embodiment, the polymer component forms no micelles under the conditions of use of the formulation. No CMC (critical micellar concentration) is reached.

Polymer components technically preferred for the process are those which are melt-processable.

It is preferred for at least one polymer of the polymer component to be selected from:

synthetic polymers such as polyvinyllactams, in particular polyvinylpyrrolidone (PVP); copolymers of vinyllactams such as N-vinylpyrrolidone, N-vinylpiperidone and N-vinyl-$\epsilon$-caprolactam, but especially N-vinylpyrrolidone, with (meth)acrylic acid and/or (meth)acrylic esters, such as long-chain (meth)acrylates, e.g. stearyl (meth)acrylate, dialkylaminoalkyl (meth)acrylates, which may be quaternized, and maleic anhydride, vinyl esters, especially vinyl acetate, vinylformamide, vinylsulfonic acid or quaternized vinylimidazole; copolymers of vinyl acetate and crotonic acid; partially hydrolyzed polyvinyl acetate; polyvinyl alcohol; (meth)acrylic resins such as poly(hydroxyalkyl (meth)acrylates), poly(meth)acrylates, acrylate copolymers, e.g. from alkyl acrylates with (meth)acrylic acid, and copolymers of dimethylaminoethyl acrylates and methacrylic esters (e.g. Eudragit types); polyalkylene glycols such as polypropylene glycols and polyethylene glycols, preferably with molecular weights above 1 000, particularly preferably above 2 000 and very particularly preferably above 4 000 (e.g. polyethylene glycol 6 000); polyalkylene oxides such as polypropylene oxides and, in particular polyethylene oxides, preferably of high molecular weight, especially with weight average molecular weights of more than 100 000; copolymers of methyl methacrylate and acrylic acid; polyacrylamides, polyvinylformamide (where appropriate partially or completely hydrolyzed);

modified natural polymers, e.g. modified starches and modified celluloses, such as cellulose esters and, preferably cellulose ethers, e.g. methylcellulose and ethylcellulose, hydroxyalkylcelluloses, in particular hydroxypropylcellulose, hydroxyalkylalkylcelluloses, in particular hydroxypropylmethylcellulose or hydroxypropylethylcellulose, cellulose phthalates, in particular cellulose acetate phthalate and hydroxypropylmethylcellulose phthalate; and natural or predominantly natural polymers such as gelatin, polyhydroxyalkanoates, e.g. polyhydroxybutyric acid and polylactic acid, polyamino acids, e.g. polylysine, polyasparagine, polydioxanes and polypeptides, and mannans, especially galactomannans.

Of these, the modified natural and, in particular, the synthetic polymers are preferred.

It is particularly preferred for at least one polymer of the polymer component to be selected from polyvinylpyrrolidones, vinylpyrrolidone/vinyl acetate copolymers, hydroxyalkylcelluloses, hydroxyalkylalkylcelluloses, cellulose phthalates, polyalkylene glycols, (meth)acrylic resins: for example the polyvinylpyrrolidones having the proprietary name Kollidon® and weight average molecular weights of about 2 000 to about $1.5 \times 10^6$, for example the polyvinylpyrrolidone having the proprietary name Kollidon® 17 PF and a weight average molecular weight of about 7 000 to about 11 000; vinylpyrrolidone/vinyl acetate copolymers, in particular with a vinylpyrrolidone:vinyl acetate ratio of from about 30:70 to about 70:30, for example the product having the proprietary name Kollidon® VA 64 and a vinylpyrrolidone:vinyl acetate ratio of about 60:40; hydroxyalkylcelluloses with 1 to 3 carbon atoms in the alkyl moiety, in particular hydroxypropylcellulose, for example the hydroxypropylcellulose having the proprietary name Klucel®; hydroxyalkylalkylcelluloses with 1 to 3 carbon atoms in the alkyl moieties; in particular hydroxypropylmethylcellulose, for example the methylcellulose and methylcellulose derivative mixtures having the proprietary name Methocel® and containing ethyl, hydroxyethyl, hydroxypropyl and carboxymethyl ether groups, cellulose phthalates, especially hydroxypropylmethylcellulose phthalate, polyalkylene glycols with 2 and/or 3 carbon atoms in the alkylene moiety, especially polyethylene glycols, for example the polyethylene glycols having the proprietary name Lutrol® and weight average molecular weights of from 2 000 up to about 20 000, and polypropylene glycols, copolymers based on dimethylaminoethyl methacrylate and methacrylic esters such as methyl methacrylate and butyl methacrylate, for example the acrylic resins having the proprietary name Eudragit® E and based on dimethylaminoethyl methacrylate, methyl and butyl (meth)acrylate with weight average molecular weights of about 150 000, copolymers with anionic characteristics based on methacrylic acid and methyl methacrylate, for example the acrylic resins having the proprietary names Eudragit® L and S and with weight average molecular weights of 250 000 and 135 000, respectively.

Very particular preference is given to the aforementioned polyvinylpyrrolidones and cellulose derivatives, especially Kollidon® VA 64 and low molecular weight hydroxypropylcellulose, e.g. Klucel® EF with weight average molecular weights of about 45 000 to about 70 000 or about 80 000, and hydroxypropylmethylcellulose, e.g. Methocel® E3, E5 and E7.

The polymer component of formulations of the invention preferably comprises at least one of the polymers described above. It may contain other polymers of these types and/or other types. The properties of the formulation of the invention can be altered by nature of the polymer chosen or the admixture of different polymers. In particular, it is possible in this way to control the release of active ingredient.

In one embodiment of the present invention, the polymer component consists of one of the polymers described above. In another embodiment of the present invention, the polymer component consists of a mixture of at least two of the polymers described above.

Polymers which are advantageous for use as polymeric binder are those which have a K value (according to H. Fikentscher, Cellulose-Chemie 13 (1932), pp. 58-64 and 71-74) in the range between 10 and 100, in particular between 15 and 80.

The content of the polymer component in the solid formulation of the invention is usually 5 to 96% by weight, preferably 10 to 80% by weight, and in particular 20 to 70% by weight.

Formulations of the invention may, besides polymer component and lipid component, contain further pharmaceutically acceptable excipients (excipient component iv). Such excipients may facilitate production of the formulation and/or modulate its properties. The nature and amount are advantageously chosen so that they do not impair development of the special properties of the formulations of the invention and of a molecular dispersion which is present where appropriate, in particular a solid solution, or do not contribute to destabilizing this system.

Excipients are, for example, conventional pharmaceutical excipients, the total amount of which may be up to 100% by weight based on the polymer component, for example, fillers such as the abovementioned sugar alcohols, e.g. mannitol, sorbitol, xylitol and isomalt (cf. DE 195 36 394), talc, sucrose, lactose, cereal or corn starch, potato flour, where present in particular in a concentration of 0.02 to 50, preferably 0.20 to 20, % by weight based on the total weight of the mixture;

lubricants, glidants and mold release agents such as magnesium, aluminum and calcium stearates, talc and silicones, and animal or vegetable fats, especially in hydrogenated form and those which are solid at room temperature. These fats preferably have a melting point of 30° C. or above. Technically preferred in relation to the melt extrusion process are—as described in DE 197 31 277—triglycerides of $C_{12}$, $C_{14}$, $C_{16}$ and $C_{18}$ fatty acids or—to improve the processing properties—lecithin, as described in connection with the extrusion of an isomalt-containing polymer/active ingredient melt in DE 195 36 394. It is also possible to use waxes such as carnauba wax. These fats and waxes may advantageously be admixed alone or together with mono- and/or diglycerides or phosphatides, in particular lecithin. The mono and diglycerides are preferably derived from the abovementioned fatty acid types. The lipids which are present according to the invention normally carry out the function of these excipients, so that only small amounts and, advantageously, no lubricants, glidants and mold release agents are added as excipients to the formulation. Where present, the total amount of excipients in the form of lubricants and mold release agents is preferably 0.1 to 10% by weight and, in particular, 0.1 to 1% by weight, based on the total weight of the mixture;

flow regulators, e.g. diatomaceous earths, especially the high-purity silicon dioxides having the proprietary name Aerosil®, where present in particular in an amount of 0.1 to 5% by weight based on the total weight of the mixture;

dyes such as azo dyes, organic or inorganic pigments or dyes of natural origin, with preference being given to inorganic pigments where present in a concentration of 0.001 to 10, preferably 0.5 to 3% by weight based on the total weight of the mixture;

stabilizers such as antioxidants, light stabilizers, hydroperoxide destroyers, radical scavengers, stabilizers against microbial attack;

plasticizers, especially those described below.

It is also possible to add wetting agents, preservatives, disintegrants, adsorbents and mold release agents, and surfactants, especially anionic and nonionic, such as, for example, soaps and soap-like surfactants, alkyl sulfates and alkylsulfonates, salts of bile acids, alkoxylated fatty alcohols, alkoxylated alkylphenols, alkoxylated fatty acids and fatty acid glycerol esters, which may be alkoxylated, and solubilizers such as Cremophor (polyethoxylated castor oil), Gelucire, vitamin E TPGS and Tween (ethoxylated sorbitan fatty acid esters) (cf., for example, H. Sucker et al. Pharmazeutische Technologie, Thieme-Verlag, Stuttgart 1978). Since the formulations of the invention form emulsions on contact with water or aqueous solvents, it is possible to keep the addition of surface-active excipient, in particular substances with high HLB values, especially of more than 8, 10 and, in particular, above 15, low, usually in amounts of less than 1% by weight. It is possible and advantageous to dispense with such an addition.

Excipients for the purpose of the invention also mean substances for producing a solid solution with the active pharmaceutical ingredient. Examples of these excipients are pentaerythritol and pentaerythritol tetraacetate, urea, phosphatides such as lecithin, and sugar alcohols such as xylitol and mannitol, citric and succinic acids, bile acids, stearins and others as indicated, for example, by J. L. Ford, Pharm. Acta Helv. 61, (1986), pp. 69-88.

Also regarded as pharmaceutical excipients are additions of acids and bases to control the solubility of an active ingredient (see, for example, K. Thoma et al., Pharm. Ind. 51, (1989), pp. 98-101).

Excipients in the sense of the invention are also vehicles specific for the drug form, i.e. appropriate for a particular drug form, in particular oral and, especially, tablets and capsules, also low-melting or liquid excipients such as polyalkylene glycols of low molecular weight, in particular polyethylene glycol and/or polypropylene glycol with weight average molecular weights of less than 1 000, water or suitable aqueous systems.

It is also possible to add excipients such as masking flavors and odor-masking agents, in particular sweeteners and odorants.

An embodiment of this type is based on expert knowledge as described, for example, in Fiedler, H. B., Lexikon der Hilfsstoffe für Pharmazie, Kosmetik, und angrenzende Gebiete, 4th edition, Aulendorf: ECV-Editio-Cantor-Verlag (1996).

The excipient component in solid formulations of the invention preferably comprises at least one of the other excipients described above. It may comprise other excipients of these types and/or other types.

One embodiment of the present invention comprises formulation bases with excipient component. In this case, the content of other pharmaceutically acceptable excipients in the formulations of the invention can be up to 91% by weight, preferably up to 60% by weight and, in particular, up to 40% by weight.

A particular embodiment of the present invention comprises formulations which comprise
i) low molecular weight heparin, in particular one with a weight average molecular weight of about 500 to about 10 000;
ii) at least one unsaturated fatty acid, which is preferably selected from oleic acid, linoleic acid and/or linolenic acid, or corresponding mono- or diglycerides;
iii) at least one polymer selected from polyvinylpyrrolidones, vinylpyrrolidone copolymers, in particular with vinyl acetate, or cellulose derivatives, in particular hydroxypropylcelluloses and hydroxypropylmethylcelluloses; and
iv) where appropriate other excipients, for example a flow regulator.

The formulations of the invention preferably contain less than 5% by weight and, in particular, less than 1% by weight of water. A particular embodiment is represented by essentially anhydrous formulations.

The formulations of the invention preferably have a solid consistency. The term "solid" has in this connection the meaning assigned in appropriate pharmacopeias in connection with pharmaceutical preparations. Formulations of the invention may also be of semisolid or viscous liquid consistency. The terms "semisolid" and "viscous liquid" also have within the framework of the present invention the meanings assigned in appropriate pharmacopeias in connection with pharmaceutical preparations. For example, formulations of the invention may be of semisolid consistency if the contents of lipids and, in particular low-melting lipids are relatively high. A semisolid and, if desired, also viscous liquid consistency can, as is well known, also be achieved by adding suitable excipients, in particular low-melting or liquid vehicles.

The present invention therefore also relates to the use of formulations of the invention as drug form for the oral administration of at least one heparin, glucosaminoglycan or heparinoid.

Accordingly, formulations of the invention are mainly used in the pharmaceutical, both human and veterinary medical, sector. In this sense, the formulations are used as or in drug forms, i.e. the formulations of the invention have expedient forms appropriate for pharmaceutical practice, if necessary together with other excipients.

Thus, the term "drug form" refers to any dosage form for administration of active ingredients to an organism, preferably to mammals, in particular humans, and also agricultural or domestic animals.

Conventional drug forms include, in particular, (in alphabetical sequence) emulsions and microemulsions, granules, capsules, pellets, powders, suspensions, suppositories, tablets, especially coated tablets.

Emulsions and microemulsions may be of the oil-in-water or water-in-oil type and contain the formulations of the invention as disperse or dispersing phase. These emulsions or microemulsions may be stabilized by the presence of emulsifiers known to be used for this purpose. One advantage of formulations of the invention is, however, usually only small amounts of emulsifier are added and, in a particular embodiment of the present invention, it is possible to dispense with addition of emulsifiers, in particular O/W emulsifiers with HLB values over 10 and, in particular, over 15.

Granules consist of solid grains of formulations of the invention, each grain representing an agglomerate of powder particles. Granules are preferably intended for oral use as drug form. The user can be offered single-dose preparations, for example granules packed in a small bag (sachet), a paper bag or a small bottle, or multidose preparations which require appropriate dimensions. However, in many cases, such granules do not represent the actual drug form, but are intermediates in the manufacture of particular drug forms, for example tablet granules to be compressed to tablets, capsule granules to be packed into hard gelatin capsules, or instant granules or granules for oral suspension to be put in water before intake.

As capsules, the formulations of the invention are usually packed into a hard shell composed of two pieces fitted together or a soft, one-piece, closed shell, which may vary in shape and size. It is likewise possible for formulations of the invention to be encased or enveloped or embedded in a matrix in suitable polymers, that is to say microcapsules and microspherules. Hard and soft capsules consist mainly of gelatin, while the latter have a suitable content of plasticizing substances such as glycerol or sorbitol. Hard gelatin capsules are used to receive formulations of the invention which have a solid consistency, for example granules, powder or pellets. Soft gelatin capsules are particularly suitable for formulations with a semisolid consistency and, if required, also viscous liquid consistency.

Pellets are granules of formulations of the invention in the particle size range from about 0.5 to 2 mm in diameter. Both with a narrow particle size distribution, preferably from 0.8 to 1.2 mm, and with an essentially round shape, are preferred.

In semisolid preparations, formulations of the invention are taken up in a suitable vehicle. Appropriate bases are known to the pharmaceutical technologist.

Suppositories are solid preparations for rectal, vaginal or urethral administration. In order to be appropriate for the administration route, formulations of the invention in these drug forms are usually taken up in suitable vehicles, for example in fats which melt at body temperature, such as hard fat, macrogols, i.e. polyethylene glycols with molecular weights of 1 000 to 3 000 in various proportions, glycerol gelatin and the like.

Tablets are solid preparations in particular for oral use. The meaning of oral within the framework of the present invention is, in particular, that of the term "peroral", i.e. tablets for absorption or action of the active ingredient in the gastrointestinal tract. Particular embodiments are coated tablets, layered tablets, laminated tablets, tablets with modified release of active ingredient, matrix tablets, effervescent tablets, chewable tablets or pills. The formulations of the invention usually comprise at least a part of the necessary tablet excipients, such as binders, fillers, glidants and lubricants, and disintegrants. Tablets of formulations of the invention may also if necessary comprise other suitable excipients. Mention should be made in this connection of excipients which assist tableting, for example lubricants and glidants, for example those mentioned above, with preference for magnesium stearate in particular for facilitating compaction.

Coated tablets additionally comprise suitable coating materials, for example film coating agents or coating aids, especially those mentioned below. Coated tablets include, in particular, sugar-coated tablets and film-coated tablets.

Powders are finely dispersed solids of formulations of the invention with particle sizes usually of less than 1 mm. The above statements about granules apply correspondingly.

Preference is given according to the invention to capsules packed with comminuted granules, powders or pellets of formulations of the invention, instant granules and granules for oral suspension composed of formulations of the invention with addition of masking flavors, and, in particular, tablets.

The drug forms of the invention are usually packed in a suitable form. Pushout packs made of plastic and/or metal for solid drug forms are frequently used.

The present invention also relates to a process for producing a formulation of the invention by mixing components i), ii), iii) and, where appropriate, iv) to form a plastic mixture. Thus, to form the plastic mixture, at least two measures are necessary, on the one hand the mixing of the components forming the mixture, and on the other hand the plastication thereof, i.e. the conversion thereof into the plastic state. These measures may take place for one or more components or portions of components successively, intermeshingly, alternately or in another way. Accordingly, it is possible in principle for the conversion into the plastic state to take place concurrently during a mixing process, or for the mixture first to be mixed and then to be converted into the plastic state. A plurality of plastic mixtures differing in composition may be formed during a process and are mixed together and/or with other components or portions of components. For example, a premix of a portion of the components, e.g. lipid component and polymer component, can be granulated to form a plastic mixture, and the granules can then be converted, with the addition of other components, e.g. the active ingredient component, into another plastic mixture whose composition may correspond to that of the formulation. It is also possible for all the components first to be combined and then either converted into the plastic state at the same time of the mixing or first mixed and then converted into the plastic state.

The formation of a plastic mixture can take place by melting or—with additional input of mechanical energy, e.g. by kneading, mixing or homogenizing—else below the melting point of the mixture. The plastic mixture is preferably formed at temperatures below 220° C. The formation of the plastic mixture usually does not take place by one or more components being converted into a paste or partially dissolved with liquids or solvents, but takes place mainly or exclusively by thermal or thermal/mechanical action on the component(s), i.e. by thermal plastication. The plastic mixture is preferably formed by extrusion, particularly preferably by melt extrusion. The plastication process steps can be carried out in a manner known per se, for example as described in EP-A-0 240 904, EP-A-0 337 256, EP-A-0358 108, WO 97/15290 and WO 97/15291. The contents of these publications and, in particular, the statements about melt extrusion present therein are incorporated herein by reference.

It should be possible to convert the polymer component into a plastic state in the complete mixture of all the components in the range from 30 to 200° C., preferably 40 to 170° C. The glass transition temperature of the mixture should therefore be below 220° C., preferably below 180° C. If necessary, it is reduced by conventional, pharmacologically acceptable plasticizing excipients.

Examples of such plasticizers are:

organic, preferably involatile compounds, such as, for example, $C_7$-$C_{30}$-alkanols, ethylene glycol, propylene glycol, glycerol, trimethylolpropane, triethylene glycol, butandiols, pentanols such as pentaerythritol and hexanols, polyalkylene glycols, preferably having a molecular weight of from 200 to 1 000, such as, for example, polyethylene glycols, polypropylene glycols and polyethylene/propylene glycols, silicones, aromatic carboxylic esters (e.g. dialkyl phthalates, trimellitic esters, benzoic esters, terephthalic esters) or aliphatic dicarboxylic esters (e.g. dialkyl adipates, sebacic esters, azelaic esters, citric and tartaric esters), fatty acid esters such as glycerol mono-, di- or triacetate or sodium diethyl sulfosuccinate. The concentration of plasticizer is, where present, generally 0.5 to 30, preferably 0.5 to 10, % by weight based on the total weight of polymer and plasticizer.

The amount of plasticizer advantageously does not exceed 30% by weight based on the total weight of polymer and plasticizer so that—in the area of solid forms—storage-stable formulations and drug forms showing no cold flow are formed. It is usually unnecessary to add a plasticizer for the purpose of plastication because the lipid component present according to the invention has plasticizing properties.

The process of the invention can advantageously be carried out at temperatures below 200° C. and preferably below 170° C., but above room temperature (25° C.), preferably above 40° C. A preferred temperature range for the extrusion of formulations of the invention is 80 to 150° C. The process is carried out in particular in a temperature range extending 40° C., preferably 30° C., and particularly preferably 20° C., upward or downward from the softening point of the mixture of the components.

In certain cases it may be advantageous to add components or portions of components as solution or suspension in a solvent. Particularly expedient ones are low molecular weight volatile solvents, e.g. water, $C_1$-$C_6$-monoalcohols and ethers thereof, esters of $C_1$-$C_6$-monoalkanols with $C_1$-$C_6$-carboxylic acids, alkanes. Another solvent which can be used is liquid $CO_2$. Water-soluble active ingredients can be employed as aqueous solution or, preferably, be taken up in an aqueous solution or dispersion of the polymer component or a portion thereof. Corresponding statements apply to active ingredients which are soluble in one of the solvents mentioned, if the liquid form of the components used is based on an organic solvent. The components to be employed according to the invention may contain small amounts of solvent, e.g. because of hygroscopicity, trapped solvent or water of crystallization. The total solvent content of the plastic mixture is preferably less than 15%, in particular less than 10%, and particularly preferably less than 5%. The plastic mixture is preferably formed without the addition of a solvent, i.e. in particular in particular by solvent-free melt extrusion.

The components, i.e. active ingredient, lipid and polymer and, where appropriate, other excipients, can first be mixed and then be converted into the plastic state and homogenized. This can be done by operating the apparatuses such as stirred vessels, agitators, solids mixers etc. alternately. Sensitive active ingredients can then be mixed in (homogenized), preferably in "intensive mixers" in plastic phase with very small residence times. The active ingredient(s) may be employed as such, i.e. in particular in solid form, or as solution, suspension or dispersion.

In particular embodiments of the process of the invention it may be advantageous for the active ingredient and lipid first to be mixed and then to be added to the plasticated polymer. This procedure may be advantageous in particular when active ingredient and/or lipid are thermally unstable.

The plastication, melting and/or mixing takes place in an apparatus usual for this purpose. Extruders or heatable containers with agitator, e.g. kneaders (like those of the type mentioned hereinafter) are particularly suitable.

It is also possible to use as mixing apparatus those apparatuses which are employed for mixing in plastics technology. Suitable apparatuses are described, for example, in "Mischen beim Herstellen und Verarbeiten von Kunststoffen", H. Pahl, VDI-Verlag, 1986. Particularly suitable mixing apparatuses are extruders and dynamic and static mixers, and stirred vessels, single-shaft stirrers with stripper mechanisms, especially paste mixers, multishaft stirrers, especially PDSM mixers, solids mixers and, preferably, mixer/kneader reactors (e.g. ORP, CRP, AP, DTB from List or Reactotherm from Krauss-Maffei or Ko-Kneader from Buss), trough mixers or internal mixers or rotor/stator systems (e.g. Dispax from IKA).

The process steps of mixing and plastication, that is to say in particular the melting, can be carried out in the same apparatus or in two or more apparatuses operating separately from one another. The preparation of a premix can be carried out in one of the mixing apparatuses described above and normally used in particular for granulation. Such a premix can then be fed directly for example into an extruder, and then be extruded where appropriate with the addition of other components.

It is possible in the process of the invention to employ as extruders single screw machines, intermeshing screw machines or else multiscrew extruders, especially twin screw extruders, corotating or counter-rotating and, where appropriate, equipped with kneading disks. If it is necessary in the extrusion to evaporate a solvent, the extruders are generally equipped with an evaporating section. Examples of extruders which can be used are those of the ZSK series from Werner & Pfleiderer.

The mixing apparatus is charged continuously or batchwise, depending on its design, in a conventional way. Powdered components can be introduced in a free feed, e.g. via a weigh feeder. Plastic compositions can be fed in directly from an extruder or via a gear pump, which is particularly advantageous if the viscosities and pressures are high. Liquid media can be metered in by a suitable pump unit.

The lipid component can—as described above—be incorporated continuously or batchwise into the formulation. Thus, at least part of the polymer component (matrix) can first be used as support for at least part of the lipid component, and then be formulated according to the invention as premix to form a plastic mixture, possibly with addition of other ingredients, preferably by extrusion. Continuous addition of at least part of the lipid component to a plastic mixture is preferred. This is particularly preferred when the lipids to be used according to the invention can be processed in semisolid or liquid form. Accordingly, the lipids described above and having relatively low melting points are also preferred for technical reasons in the process, and of these in turn preference is given to those which at room temperature, i.e. about 20 to 30° C., are of semisolid (waxy), and preferably of liquid (oil) consistency. It is preferred for these to be metered directly into the mixing apparatus, in particular an extruder. This may save a granulation step to be carried out separately.

The mixture which has been obtained by mixing and converting the polymer component, the active ingredient component, the lipid component and, where appropriate, other excipients into the plastic state is pasty, of high viscosity or low viscosity (thermoplastic) and can therefore also be extruded. The glass transition temperature of the mixture is advantageously below the decomposition temperature of all the components present in the mixture.

The formulation of the invention is suitable as plastic mixture—where appropriate after cooling or solidification—in particular as extrudate, for all conventional processes for manufacturing conventional drug forms.

The present invention also relates to a process for producing drug forms of formulations of the invention, where the formulation can be produced by the above process, and the formulation is converted into the required drug form where appropriate with the addition of other excipients. This can be done by using shaping process measures such as shaping the plastic mixture, in particular by extrusion or melt extrusion, and shaping the plastic mixture, in particular the extrudate—where appropriate after cooling or solidification—for example by granulation, grinding, compression, casting, injection molding, tableting under pressure, tableting under pressure with heat. It is also possible to convert a formulation into a desired drug form by introducing it into suitable vehicles. It is thus also possible to process solid formulations into semisolid or liquid formulations through the addition of suitable vehicles.

A large number of, in particular solid, drug forms can be manufactured in this way. For example, powders or granules can be produced by grinding or chopping the solidified or at least partly solidified plastic mixture, and can be either used directly for treatment or, where appropriate with addition of conventional excipients, further processed to the above drug forms, especially to tablets.

Drug forms are preferably shaped before solidification of the plastic mixture and result in a form which can be employed for treatment where appropriate after coating in a conventional way.

The shaping to the drug form before solidification can take place in a variety of ways depending on the viscosity of the plastic mixture, for example by casting, injection molding, compression, nipping or calendering. This is done by conveying the plastic mixture described above in the process according to the invention to one or more shaping steps. The conveying can take place by pressing, pumping, e.g. with gear pumps, or, preferably, with an extruder.

The plastic mixture is particularly preferably formed in one or more, preferably one, extruder and conveyed by the latter or a downstream extruder to the shaping steps. It has proved to be advantageous in many cases to extrude on a downward incline and/or where appropriate provide a guide channel for transporting the extrudate, in order to ensure safe transport and prevent rupture of the extrudate.

It may also be advantageous, depending on the number and compatibility of the active ingredients to be employed, to employ multilayer extrudates, for example coextrudates, as described in WO 96/19963, in the process of the invention.

Multilayer solid drug forms can be produced in particular by coextrusion, in which case a plurality of mixtures of one or more of the components described above are conveyed together into an extrusion die so that the required layer structure results. Different polymers are preferably used for different layers.

Multilayer drug forms preferably comprise two or three layers. They may be in open or closed form, in particular as open or closed multilayer tablets.

If the shaping takes place by coextrusion, the mixtures from the individual extruders or other units are fed into a common coextrusion die and extruded. The shape of the coextrusion dies depends on the required drug form. Examples of suitable dies are those with a flat orifice, called slit dies, and dies with an annular orifice cross section. The design of the die depends on the formulation base used and, in particular, the polymer component and the desired drug form.

The first shaping step advantageously takes place when the extrudate emerges from the extruder through suitably shaped dies, draw plates or other orifices, for example through a breaker plate, a circular die or a slit die. This usually results in a continuous extrudate, preferably with a constant cross section, for example in the form of a ribbon or of a strand, preferably with a circular, oval, rounded or flat and broad cross section.

Suitable downstream shaping steps for extrudates are, for example, cold cut, that is to say the cutting or chopping of the extrudate after at least partial solidification, hot cut, that is to say the cutting or chopping of the extrudate while still in the plastic form, or pinching off the still plastic extrudate in a nip device. It is possible with hot or cold cut to obtain, for example, granules (hot or cold granulation) or pellets. Hot granulation usually leads to drug forms (pellets) with a diameter of from 0.5 to 3 mm, while cold granulation normally leads to cylindrical products with a length to diameter ratio of from 1 to 10 and a diameter of from 0.5 to 10 mm. It is possible in this way to produce monolayer but also, on use of coextrusion, open or closed multilayer drug forms, for example oblong tablets, pastilles and pellets. The drug forms can be provided with a coating by conventional methods in a downstream process step. Suitable materials for film coatings are the polymers mentioned as polymeric binders, in particular polyacrylates such as the Eudragit® types, cellulose esters such as the hydroxypropylcellulose phthalates, and cellulose ethers such as ethylcellulose, hydroxypropylmethylcellulose or hydroxypropylcellulose, and gelatin. Further shaping steps may also follow, such as, for example, rounding off the pellets obtained by hot or cold cut using rounding-off devices as described in DE-A-196 29 753.

It is particularly preferred for all the shaping steps to be carried out on the still plastic mixture or still plastic extrudate. Besides hot cut, where appropriate with subsequent rounding off, a particularly suitable process is one in which the plastic mixture is shaped to the dosage form in a molding calender. This is done by conveying a still plastic mixture or a still plastic extrudate to a suitable molding calender. Suitable molding calenders usually have molding rolls and/or belts for the shaping, with at least one of the molding rolls and/or at least one of the belts have depressions to receive and shape the plastic mixture. It is preferred to use a molding calender with counter-rotating molding rolls, with at least one of the molding rolls having on its surface depressions to receive and shape the plastic mixture. Suitable molding calenders and devices containing molding rolls are generally disclosed for example in EP-A-0 240 904, EP-A-0 240 906 and WO 96/19962, and suitable belts and devices containing belts are generally disclosed for example in EP-A-0 358 105, which are expressly incorporated herein by reference.

The shaping of the still plastic mixture or still plastic extrudate preferably takes place at melt temperatures below 220° C., particularly preferably below 180° C. and very particularly preferably below 150° C., such as, for example, in the temperature ranges necessary to form the plastic mixture or at lower temperatures. If the shaping takes place at lower temperatures, it advantageously takes place at from 5 to 70° C., preferably 10 to 50° C. and particularly preferably 15 to 40° C. below the highest temperature reached on formation of the plastic mixture, but preferably above the solidification temperature of the plastic mixture.

The production according to the invention of the formulations and preparation of the drug forms can be carried out wholly or partly under sterile operating conditions, for example in cleanrooms and with use of sterilized equipment such as, for example, weighers, mixers, extruders and shaping machines, such as calenders, nip devices and choppers. It is possible either for the starting materials to be introduced into the process in sterilized form, where appropriate with the addition of suitable antibacterial and/or antiviral excipients, and/or for the process conditions, especially the temperature, to be chosen such that sterile formulations or drug forms are obtained. The resulting sterile dosage forms can then be packaged directly, likewise under sterile conditions, for example by blister packing or sealing.

The shaping and the packaging may also be carried out at the same time, in particular when the shaping of the plastic mixture by calendering is carried out by molding rolls. This is done by introducing, in addition to the plastic mixture, materials in the form of sheets between the melt and the molding roll in each case, whereby it is possible to achieve at the same time as the shaping of the plastic mixture to dosage forms an enveloping and/or a packaging of the dosage form, as described in WO-96/19963, which is incorporated herein by reference.

The present invention further relates to the use of a formulation base of the invention for administration and in particular for oral administration of at least one active ingredient, which is soluble in water, especially heparin, glycosaminoglycan or heparinoid. The purpose of this use is, in particular, to improve the pharmacological effect of the active ingredient component. Thus, this use comprises in particular a process for improving the pharmacological effect of the active ingredient component, for administration and in particular for oral administration of at least one heparin, glycosaminoglycan or heparinoid, with use of a formulation base of the invention. This entails introducing at least one heparin, glycosaminoglycan or heparinoid into this formulation base, preferably using one of the processes described above. In particular, the polymer matrix of the formulation base serves to receive at least one lipid in the production of a solid formulation of the invention to improve the pharmacological effect of the active ingredient component. The improvement in the pharmacological effect particularly applies to the oral administration of the heparin-, glycosaminoglycan- and/or heparinoid-containing formulation base to a mammal, in particular a human, an agricultural or domestic animal.

The polymer matrix is formed by the polymer component described above or at least a part thereof. At least one lipid, which is a constituent of the lipid component described above, is taken up in this polymer matrix. It is particularly preferred for the taking up to result in an essentially molecular dispersion of lipid in the polymer matrix. A homogeneous distribution of lipid in the matrix is advantageous, especially in relation to the active ingredient-promoting properties of the lipid. These advantages can be achieved even without the active ingredient being in a molecular dispersion. Lipids which can be used to improve the pharmacological effect of the active ingredient are known to the skilled worker, inter alia as absorption promoters. He is able to select at least part of the lipid component for example from among them. In addition, reference is made to the statements above in connection with the description of the lipid component.

The use according to the invention is particularly advantageous whenever active ingredients are to be administered in such a way that an active ingredient-promoting effect may occur on simultaneous administration of lipids. This relates in particular to routes of administration which include the gastrointestinal tract, that is to say, in particular, enteral, especially rectal and, preferably, oral administration. The use according to the invention is very particularly advantageous when an active ingredient to be administered can be used only inadequately by this route without suitable measures such as the addition of at least one lipid. This is the case with water-soluble active ingredients such as heparins, glycosaminoglycans and heparinoids.

Drug forms of the invention, and thus an effective amount of active ingredient, are administered to the individual to be treated, preferably a mammal, in particular a human, and also an agricultural or domestic animal. Whether such a treatment is indicated and what form it is to take depends on the individual case and is subject to medical assessment (diagnosis) which includes the signs, symptoms and/or dysfunctions which are present, the risks of developing certain signs, symptoms and/or dysfunctions, and other factors. The drug forms of the invention are usually administered one or more times a day together or alternately with other products in such a way that an individual to be treated receives a daily dose in an amount which makes therapy possible.

Formulations of the invention are mainly used as anticoagulants. This includes the prophylaxis and therapy of thromboembolic disorders, for example arterial and venous thromboses and embolisms, early and long-term treatments of myocardial infarction, in particular where there is an increased risk of thromboembolic complications, pre- and postoperative thrombosis prophylaxis to prevent thromboses in the extracorporeal circulation, for example during hemodialysis and hemofiltration, consumption coagulopathy especially in the hypercoagulation phase, and similar states in which an inhibitory effect on blood coagulation is indicated. Examples of other fields of indication are deep vein thromboses, pulmonary embolism, cardiovascular disorders, unstable angina, myocardial infarction, stroke, arrhythmia, inflammations, rheumatoid arthritis, Crohn's disease, inflammatory bowel diseases, diabetic retinopathy, diabetic nephropathy, transplant rejection, angiogenesis inhibition, metastases inhibition and cancer.

The present invention is now to be illustrated, but not restricted, by means of the following examples.

EXAMPLE 1

Figure 1:
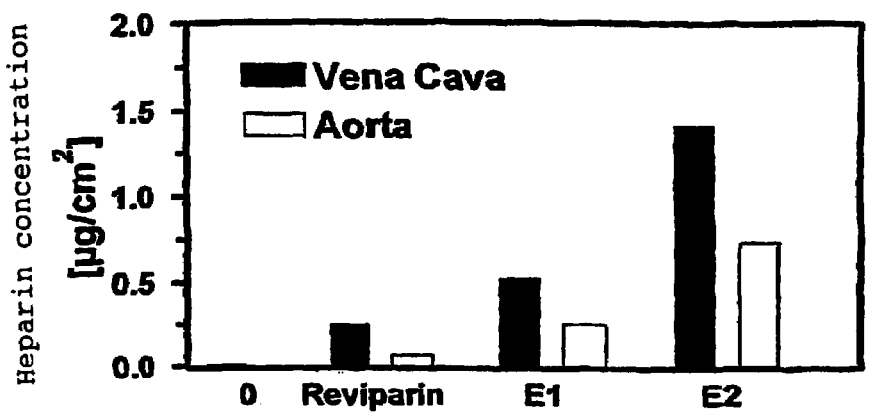
FIG. 1 shows the concentration of heparin which [lacuna] onto the endothelium of the vena cava and the abdominal aorta of male Wistar rats after intragastric administration of placebo (0), lower molecular weight heparin (reviparin) and formulations E1 and E2 of the invention.

In a laboratory twin screw extruder (from Haake, 16 mm screw diameter) a mixture of 20% by weight of LMWH (low molecular weight heparin, molecular weight distribution 2 000 to 10 000; reviparin), 64% by weight of Kollidon®VA-64, 16% by weight of oleic acid and 1% by weight of Aerosil 200 was extruded at a temperature of 110° C. to give a white homogeneous melt which, after cooling, was ground in a laboratory mill. The resulting granular powder E1 was dissolved in water to form an emulsion. The size of the emulsion droplets in this preparation was measured using a Mastersizer instrument (from Malvern, UK). 90% of the particles had sizes below 25 µm, 50% of the particles were smaller than 1.8 µm (bimodal distribution).

EXAMPLE 2

In analogy to Example 1, a mixture of 20% by weight of LMWH (low molecular weight heparin, molecular weight distribution 2 000 to 10 000; reviparin), 70% by weight of hydroxypropylcellulose (Klucel® EF), 10% by weight of oleic acid and 1% by weight of Aerosil 200 was extruded at a temperature of 130° C. A white melt was obtained and became solid after cooling, and was ground in a laboratory mill to a granular powder E2 which was soluble in water to form an emulsion. The size of the emulsion droplets in this preparation was measured using a Mastersizer instrument (from Malvern, UK). 90% of the particles had sizes below 32 µm, and 50% of the particles were smaller than 12 µm.

EXAMPLE 3

Extrusion in analogy to Example 1 but with 20% by weight of dextran sulfate (from ICN) in place of LMWH at 110° C. resulted in an ivory-colored extrudate which, after cooling, was ground in a mill.

EXAMPLE 4

Extrusion in analogy to Example 2 but with 20% by weight of dextran sulfate (from ICN) in place of LMWH at 150° C. resulted in an pale yellowish extrudate which, after cooling, was ground in a mill.

EXAMPLE 5

A mixture of 20% by weight of palmitic acid and 20% by weight of oleic acid was completely liquefied in a heated vessel at a temperature of 70° C., and 3% by weight of hydroxypropylcellulose and 57% by weight of low molecular weight heparin were homogeneously incorporated by stirring/kneading. The mixture was packed into hard gelatin capsules while still warm.

EXAMPLE 6

The Reviparin incorporated in Examples 1 and 2 originally has a specific anti-Xa activity of 136 IU/mg. The subsequent checking of the reviparin content in the extrudate took place by HPLC, and the biological activity of the extruded reviparin was measured as inhibitory effect on coagulation factor Xa by the method of TEIEN, A. N. et al.: Assay of heparin in plasma using a chromogenic substrate, Thromb. Res. 8, 413-416 (1976). Thus, it emerged that extrudates E1 and E2 with active ingredient contents of 23.4% and 17.7% respectively had activities of 31.3 IU/mg and 24.1 IU/mg respectively. This corresponds to 98 and 100%, respectively, of the original activity.

EXAMPLE 7

The melt extrudate E1 or E2, reviparin or placebo (saline solution) were administered intragastrically by gavage to male Wistar rats. 20 animals were used in each substance group. The dose of active substance was in each case 0.025 mg/kg bodyweight. 4 hours after administration of the test substances, the vena cava and abdominal aorta were removed from the animals under anesthesia. The endothelium of the blood vessels was worked up as described by Hiebert and Jaques (Artery, 2, 26, 1976). The content of endothelium-bound reviparin was determined by agarose gel electrophoresis as described by Jaques et al. (J Lab Clin Med, 115, 422, 1990). Significantly higher concentrations of reviparin were found on the endothelium after administration of E1 and E2.

EXAMPLE 8

Male Wistar rats were briefly anesthetized. After the skin above the jugular vein had been opened, 5 drops of a formalin/methanol solution were applied (10/65% by volume). As described by Blake et al. (J Clin Path, 12, 118, 1959) this chemically induces a thrombosis. 4 hours after the induction of thrombosis, the jugular vein was examined for the presence of a hard clot. 20 animals were used in each group. The extrudate E1 or E2, reviparin or placebo (saline solution) were administered intragastrically by gavage to the experimental animals 24 hours before thrombus induction. The dose was 7.5 mg/kg bodyweight.

Figure 2:
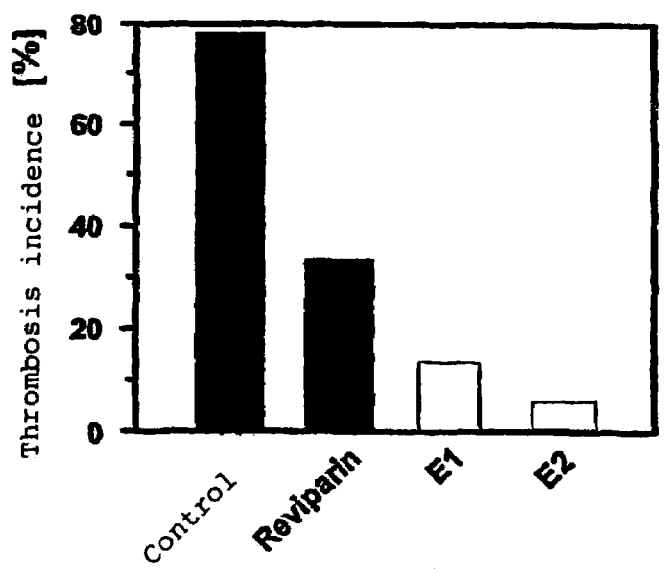
FIG. 2 shows the incidence of thromboses in male Wistar rats after administration of placebo (0), lower molecular weight heparin (reviparin) and formulations E1 and E2 of the invention.

The incidence of thromboses in each group was used for the evaluation (FIG. 2). It was found that inhibition of thrombus formation after administration of extrudate E1 and E2 was distinctly higher than after administration of reviparin alone.

We claim:

1. A solid or semisolid formulation, comprising
   i) 5-40% by weight of an active ingredient component containing at least heparin, glycosaminoglycan or heparinoid, and optionally at least one other active ingredient;
   ii) a lipid component containing at least one lipid, wherein the lipid component has a hydrophilic-lipophilic balance not exceeding 8; 10-80% by weight of a solid polymer component containing one or more polymers selected from the group consisting of a polyvinylpyrrolidone, a vinylpyrrolidone/vinylacetate copolymer, a hydroxyalkylcellulose, a hydroxyalkylalkylcellulose, a cellulose phthalate and a (meth)acrylic resin; and
   iv. optionally, at least one pharmaceutically acceptable excipient, and provided that
      when the formulation comprises water, said water is present at less than 1% by weight,
      and wherein the formulation does not contain a surface active excipient having a hydrophilic-lipophilic balance of more than 10.

2. The formulation of claim 1, wherein the heparin is a low molecular weight heparin.

3. The formulation of claim 1, wherein the active ingredient component contains less than 5% crystals.

4. The formulation of claim 3, wherein the active ingredient component is essentially free of crystals.

5. The formulation of claim 1, wherein at least one lipid in the lipid component is selected from the group consisting of a fatty acid, a triglyceride, a diglyceride and a monoglyceride.

6. The formulation of claim 5, wherein the fatty acid is unsaturated.

7. The formulation of claim 1, wherein the lipid component has a hydrophilic-lipophilic balance not exceeding 5.

8. The formulation of claim 1, wherein the lipid component has a melting point of less than 30° C.

9. The formulation of claim 1, wherein at least part of the lipid component is in the form of a molecular dispersion.

10. The formulation of claim 1, which comprises 3-50% by weight of the lipid component.

11. The formulation of claim 1, wherein the content of the lipid component does not exceed 40% by weight of the weight of the solid polymer component.

12. The formulation of claim 1, wherein at least part of the lipid component is taken up in the polymer component in the form of a molecular dispersion.

13. The formulation of claim 1, which is solid.

14. The formulation of claim 1, which is obtained by melt extrusion of a plastic mixture containing the components i), ii), iii) and optionally iv).

15. The formulation of claim 1 for use as drug form for oral administration of at least one heparin, glycosaminoglycan or heparinoid.

16. A solid formulation having a water content of less than 1% by weight, comprising:
   i) 5-40% by weight of a low molecular weight heparin with an average molecular weight of about 500 to about 10000;
   ii) at least one unsaturated fatty acid, which is selected from oleic acid, linoleic acid and/or linolenic acid, or corresponding mono- or diglycerides;
   iii) 10-80% by weight of a polymer component containing one or more polymers selected from the group consisting of a polyvinylpyrrolidone, a vinylpyrrolidone/vinylacetate copolymer, a hydroxypropylcellulose and a hydroxypropyl-methylcellulose;
   iii) optionally, at least one pharmaceutically acceptable excipient, and provided that
      when the formulation comprises water, said water is present at less than 1% by weight,
   and wherein the formulation does not contain a surface active excipient having a hydrophilic-lipophilic balance of more than 10.

17. The formulation of claim 16, which is obtained by melt extrusion of a plastic mixture containing the components i), ii), iii) and optionally iv).

18. The formulation of claim 1, wherein the formulation has at least one pharmaceutically acceptable excipient.

19. The formulation of claim 1, wherein the formulation does not contain water.

20. The formulation of claim 16, wherein the formulation has at least one pharmaceutically acceptable excipient.

21. The formulation of claim 16, wherein the formulation does not contain water.

* * * * *

UNITED STATES PATENT AND TRADEMARK OFFICE
CERTIFICATE OF CORRECTION

PATENT NO.      : 7,393,840 B2                                               Page 1 of 1
APPLICATION NO. : 10/296441
DATED           : July 1, 2008
INVENTOR(S)     : Rosenberg et al.

It is certified that error appears in the above-identified patent and that said Letters Patent is hereby corrected as shown below:

In Claim 1, col. 21, indicated line 53:
"exceeding 8; 10-80% by weight" should read --exceeding 8; iii) 10-80% by weight--

In Claim 1, col. 21, indicated line 59:
"iv. optionally" should read --iv) optionally--

Signed and Sealed this
Second Day of August, 2011

David J. Kappos
*Director of the United States Patent and Trademark Office*